Figure 1:
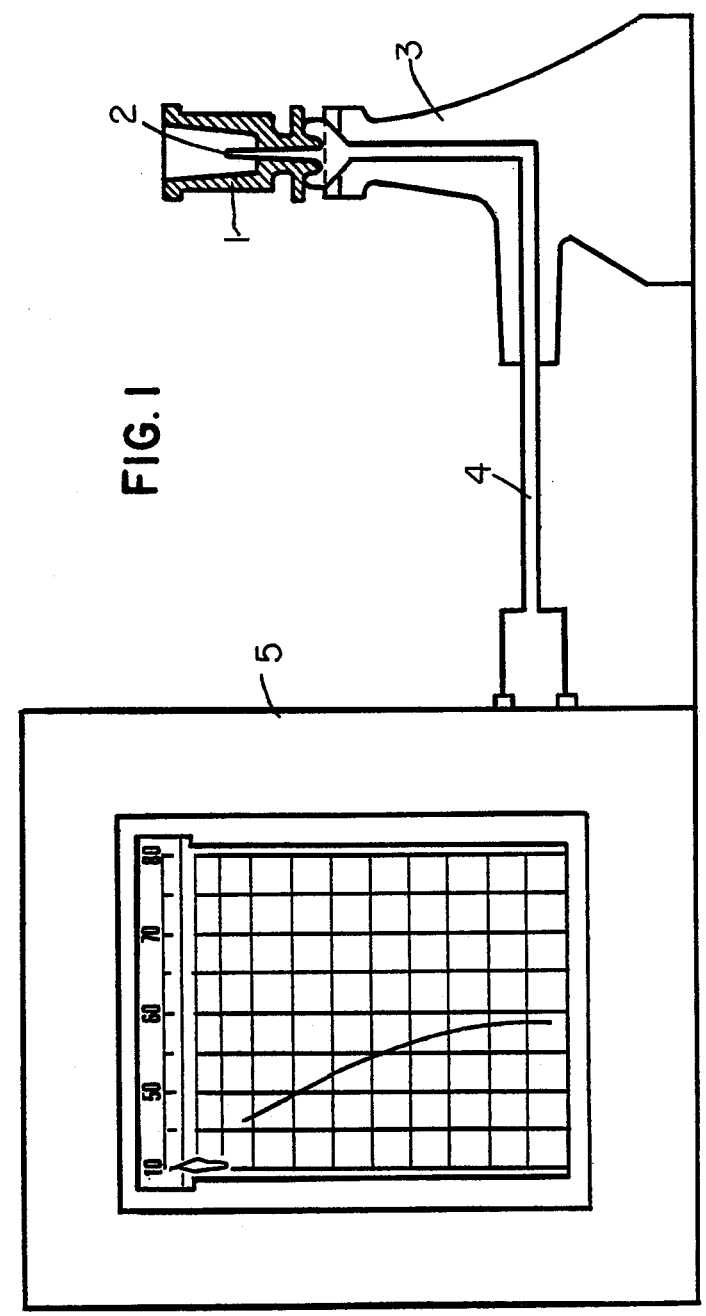

United States Patent [19]

Charbonnier

[11] 4,105,191

[45] Aug. 8, 1978

[54] CRUCIBLE FOR THE THERMAL ANALYSIS OF ALUMINUM ALLOYS

[75] Inventor: Jean Charbonnier, Herblay, France

[73] Assignee: Societe de Vente de l'Aluminium Pechiney, Paris, France

[21] Appl. No.: 810,410

[22] Filed: Jun. 27, 1977

[30] Foreign Application Priority Data

Jul. 9, 1976 [FR] France ............................ 76 22441

[51] Int. Cl.² ............................................ F27D 21/00
[52] U.S. Cl. ................................... 266/88; 266/275
[58] Field of Search ................. 266/87, 88, 89, 242, 266/275-278, 287; 432/32, 36, 156, 157, 262-265; 73/343 B, 354, 359 R, DIG. 9

[56] References Cited

U.S. PATENT DOCUMENTS

| 1,367,026 | 2/1921 | Drinker | 73/359 |
|---|---|---|---|
| 2,764,402 | 9/1956 | Newhall | 266/99 |
| 3,091,119 | 5/1963 | Fischer et al. | 266/99 |
| 3,115,781 | 12/1963 | Shearman | 73/359 |
| 3,264,874 | 8/1966 | Fischer | 266/88 |
| 3,267,732 | 8/1966 | Hance | 73/359 |

Primary Examiner—Gerald A. Dost
Attorney, Agent, or Firm—Dennison, Dennison, Meserole & Pollack

[57] ABSTRACT

A new crucible for use in the thermal analysis of metal alloys and especially aluminum alloys into which a thermocouple may be placed into a metallic thin-walled sheath which is secured in and extends upwardly from the crucible base and is connected to recording apparatus. The crucible is formed of an extremely thin-walled metallic cylindrical envelope having a base and a cake of heat-insulating material resting inside the envelope on the base, the thermocouple sheath extending upwardly through said cake.

3 Claims, 2 Drawing Figures

CRUCIBLE FOR THE THERMAL ANALYSIS OF ALUMINUM ALLOYS

The present invention relates generally to apparatus for the thermal analysis of aluminum alloys and specifically to a new crucible construction.

The control of molten metal alloys by thermal analysis consists in taking a sample of the molten metal and in allowing it to solidify under identical and reproducible conditions while recording change in temperature as a function of time. It is in fact known that in alloys consisting of a number of constituents, there is a solidification interval between the liquidus temperature (commencement of solidification) and the solidus temperature (completion of solidification). However, within this interval, temperature does not decrease in an uniform manner. The formation of a new phase is in fact evidenced by more or less sudden changes in the temperature-time curve, whereas eutectic precipitations are accompanied by flat portions in the curve. The occurrence of these phenomena and the magnitude of the flats provide information on the composition of the alloy. This procedure is at present used for controlling cast irons and steels prior to teeming. In such cases, the temperature at which solidification of the alloy begins is noted and this gives an indication of the chemical composition (carbon equivalent in cast irons and carbon content in steels).

Accordingly, an object of the invention is to provide a new crucible construction which facilitates thermal analysis of metal alloys.

A further object of the invention is to provide an analytical crucible having a low thermal inertia.

Figure 2:
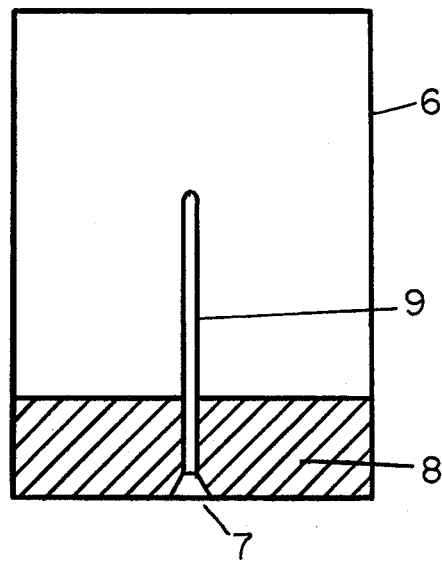

Further objects will become more apparent after review of the following specification and drawings disclosing the preferred mode of the invention, and wherein:

FIG. 1 is a front elevation, partly in section, of the crucible and related apparatus presently known in the prior art; and FIG. 2 is a front elevation partly in section of the new crucible.

For the type of measurement noted supra, use is made in the prior art of an apparatus such as that illustrated in FIG. 1. The molten metal is poured into a crucible 1, usually made of core sand, the interior of the crucible being protected. Roughly at its center, this crucible is provided with a thermocouple 2 which is inserted therein during manufacture of the crucible. Since the soldered joint of this thermocouple is in direct contact with the metal while measurement is taking place, the wire used must be relatively robust and has, for example, a diameter in the order of 0.5 mm. Sine the crucibles are used only once, they are generally designed to be fitted on a support 3 provided with pegs for ensuring contact when the crucible rests on its support, between the wires of the thermocouple and the compensation wire 4 which connects the wires of the thermocouple to the recording apparatus 5.

In the thermal analysis of aluminum alloys and particularly aluminum-silicon casting alloys having a structure approaching the eutectic, information regarding the state of transformation of the alloy are of more interest than information regarding the composition. It is in fact known that this type of alloy may have very different (transformed) metallographic structures depending upon whether elements such as sodium, calcium, phosphorus and antimony, the amounts of which are difficult to measure or which are easily eliminated, are present or not. The distinctive features of this structure are the presence or absence of primary Si, the fine or coarse Al-Si eutectic structure and the shape and size of the aluminum dendrites. These structures have a considerable influence not only upon the mechanical properties of the castings, but also upon their casting properties and, in particular, upon the size and shape of the shrinkage holes. Thus, certain castings, particularly those produced in chill molds, will only be sound if they have a well-defined structure or degree of transformation. It is therefore very important to know, immediately prior to casting, what is the state of transformation of the alloy that is about to be cast. However this state of transformation can be determined by certain parameters of the cooling curve, such as the super-cooling upon eutectic solidification, the precise temperature at the eutectic flat and the slope of the cooling curve after eutectic solidification. The variations in these parameters are smaller than in the case of ferrous alloys so that more precise measurements are necessary. It is therefore advantageous to use equipment different from that described above, so as to resolve the following problems:

(a) With the crucible described above, the quantity of heat absorbed by the crucible when it is being filled is too great. This interferes with the initial part of the curve and, sometimes may even mask the commencement of solidification (the liquidus temperature being reached even before the couple has reached the temperature of the alloy). However, even if this is not the case, the rate at which calories are released is not constant throughout solidification, and this has the drawback of rendering the refining control imprecise. This disadvantage is partially overcome by preheating the crucible, but this complicates the measurement and creates a new source of scatter.

(b) The diameter of the thermocouple is too great and this results in interference with the measurements, mainly during completion of solidification. The thermocouple in fact contributes to the release of calories probably by conduction through the wires, and in certain cases this results in the appearance of a second solidification front which is directed from the thermocouple towards the exterior. This phenomenon makes it totally impossible to predict the behavior of the alloy on shrinking, such prediction involving an appreciation of the regularity of the normal solidification front which moves inwardly from the exterior.

(c) The solidification time is too short and does not suffice to enable the phenomena to be observed.

A new apparatus has been devised and constructed which enables these problems to be resolved and which is therefore particularly suitable in the thermal analysis of aluminum alloys. This apparatus, illustrated in FIG. 2, is constituted by a small crucible 6 made of thin steel sheet, the base of which is pierced by a central hole 7. A cake 8 of heat-insulating material, for example core sand, having a thickness ranging from a few millimeters to several tens of millimeters, is placed at the bottom of this crucible. This cake holds at its center a fine metal tube 9 made of stainless steel for example, the upper end of which is closed and which acts as a protective sheath for the thermocouple used for the measurements. The lower end of the tube is embedded in the cake of core sand and does not touch the metal bottom of the crucible, so that thermal loss by way of the base of the crucible is avoided.

A sheathed thermoelectric couple is fitted within the central metallic tube in such a way that the soldered joint of this thermocouple is positioned at approximately the same level as the sealed top of the central tube.

Examples of the dimensions of the crucible are as follows: diameter — 40mm to 70mm, preferably approximately 55 mm; depth — 50 mm to 120 mm, preferably approximately 95 mm.

The sheet should be very thin, e.g., 0.1 to 1 mm and preferably 0.2 mm approximately, so that the calorific capacity is not great. For the same reason, the sheath of the thermocouple and the thermocouple itself should be of small dimensions. Preferably, use will be made of a shielded thermocouple which has a diameter of approximately 1 mm and is fitted into a sheath having a slightly greater diameter. The length of the sheath is such that its top is located roughly midway along that portion of the length of the sidewall that projects above the cake of heat-insulating material, the thickness of which is in the order of 15 mm.

Such apparatus offers the following advantages: its calorific capacity is not great; its thermal inertia is very low so that the crucible itself and the thermocouple reach temperature practically instantaneously; the "cooling" effect of the thermocouple is virtually negligible; the thermocouple is permanent and is not destroyed during each measurement, as in the previously described apparatus; and the solidification time of the sample averages 6 minutes 30 seconds, and this suffices to enable the phenomena to be fully observed.

I claim:
1. A crucible for the thermal analysis of aluminum alloys comprising:
   a metallic cylindrical envelope having a base, the cylindrical side wall extending upwardly from said base being formed solely of a thin metal sheet, a central hole being formed in the base;
   a cake of heat-insulating material at the bottom of said envelope and matching the shape thereof, said cake having an axial hole formed therein, said hole being coaxial with said central hole and forming an extension of the central hole in the base; and
   a metallic thin-walled thermocouple sheath having a sealed upper end secured in the axial hole in the cake, the sealed upper end being located roughly midway along that portion of the cylindrical side wall that extends above said cake, the lower open end of said sheath being spaced from and out of contact with the metallic base of the envelope.

2. A crucible for the thermal analysis of aluminum alloys as defined in claim 1, wherein it has the following approximate dimensions: a length in the vertical direction of 50 mm to 120 mm, a diameter of 40 to 70 mm, a thickness of the metal sheet of 0.1 to 1 mm, a diameter of the thermocouple sheath slightly in excess of 1 mm; and a thickness of the cake ranging from a new millimeters to several tens of millimeters.

3. A crucible as set forth in claim 1 and further including a thermocouple placed within the sheath in such a way that its soldered joint is located at the sealed top of the sheath, a recording apparatus, and a compensation wire interconnecting said thermocouple and said recording apparatus.

* * * * *